United States Patent [19]

Werner

[11] Patent Number: 5,377,549
[45] Date of Patent: Jan. 3, 1995

[54] ALIGNMENT DEVICE AND METHOD OF ALIGNING

[75] Inventor: F. David Werner, Bloomington, Minn.

[73] Assignee: Interlaken Technologies, Inc., Eden Prairie, Minn.

[21] Appl. No.: 991,750

[22] Filed: Dec. 17, 1992

[51] Int. Cl.⁶ .............................................. G01N 3/02
[52] U.S. Cl. ........................................ 73/860; 73/856
[58] Field of Search .......................... 73/826, 831–835, 73/837, 856–860; 81/451, 454–457; 29/464, 466, 468; 403/374, 336, 309

[56] References Cited

U.S. PATENT DOCUMENTS

| | | | |
|---|---|---|---|
| 4,137,757 | 2/1979 | Kovacs | 73/860 |
| 4,686,860 | 8/1987 | Liu | 73/856 |
| 4,721,000 | 1/1988 | Scanlon | 73/860 |
| 4,845,997 | 7/1989 | Radin et al. | 73/831 |

OTHER PUBLICATIONS

Automatic Grips, MTS Div, Minneapolis, Minn., Model 641.xx, Jan. 1965.

*Primary Examiner*—Robert Raevis
*Attorney, Agent, or Firm*—Patterson & Keough

[57] ABSTRACT

An alignment device for use with machinery in accurately aligning a machinery device train having a first and a second assembly. The alignment device comprises a central plate that has a curved surface and an opposing flat face. A disc with a curved surface is slideably engaged with the curved surface of the plate and a disc with a flat surface is slideably engaged with the flat surface of the plate. The alignment device is interposed between first and a second assemblies and preload compressive force is applied to the alignment device. Selective sliding movement of the two discs with respect to the plate, independently aligns the lateral and angular relationship of the upper and lower assemblies without the need to unload the alignment device. Maintaining the preload on the alignment device after alignment is accomplished prevents the introduction of alignment errors.

14 Claims, 4 Drawing Sheets

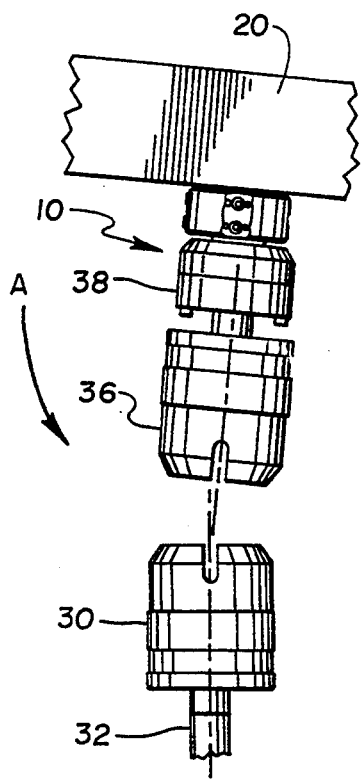
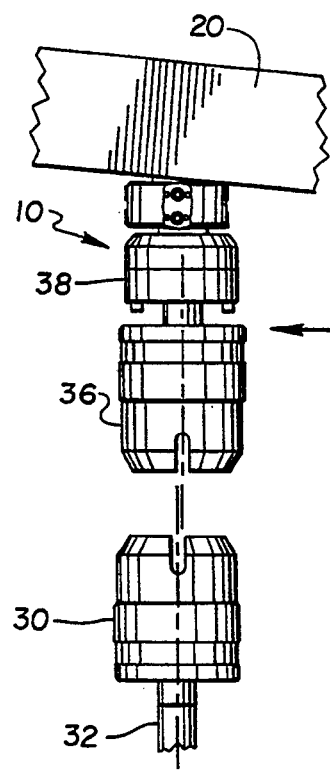
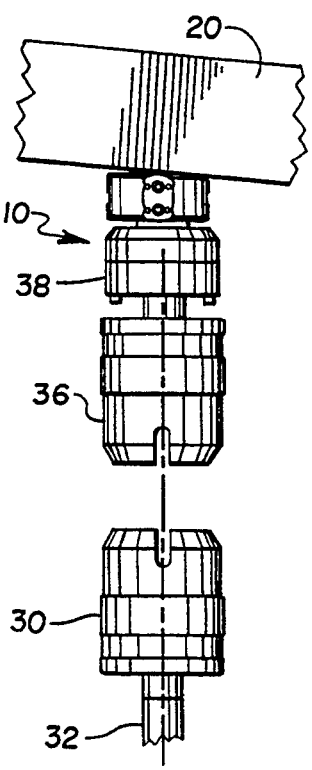
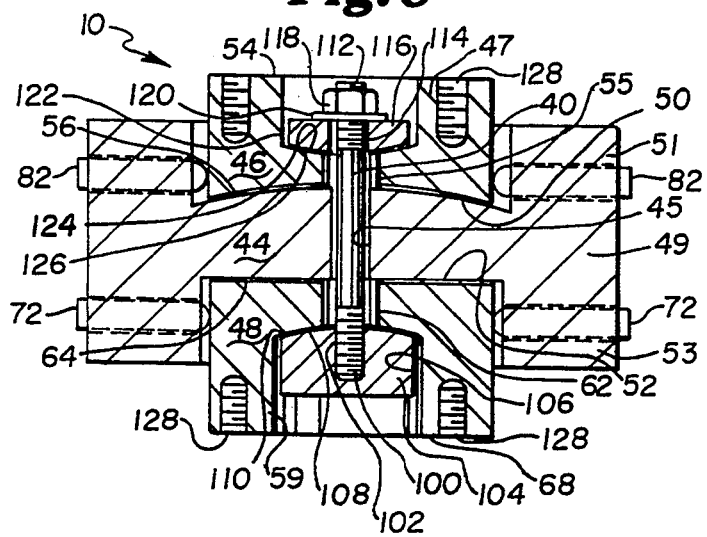

1

ALIGNMENT DEVICE AND METHOD OF ALIGNING

TECHNICAL FIELD

The present invention pertains to machine alignment where accurate alignment of a train of devices is desired and a method of aligning the train of devices. In a particular use, it pertains to materials testing equipment wherein a test specimen is held between two grips in a test frame and forces are applied to the test specimen by applying a load through the grips and to the apparatus for accurately aligning the two grips and the test specimen in the test frame. Additional uses include, for example, alignment of the output shaft of a large electric motor and the input shaft of a large pump, alignment of the workpiece and the cutting tool in a large lathe, and the alignment of the bit in relation to the workpiece in a large drill press.

BACKGROUND OF THE INVENTION

With respect to materials testing, it is often important to determine the manner in which certain parts and pieces of equipment will perform when subjected to loads and forces. In the design of the suspension system of an automobile, for example, it is important to know if a certain bolt will have the strength to safely withstand the various forces that can be expected to be imposed on it through many miles of service. The strength of such a bolt can be determined by utilizing a materials testing frame to subject a representative specimen to forces that are representative of the forces that the bolt will see in service. In this way the performance characteristics of a specific bolt are known and can be taken into account when specifying the various components that will be used in the suspension.

Further, it is important that a designer be confident that the performance specifications of a material or other part have been correctly performed and truly represent the performance that can be expected of the material or other part when in service. Accordingly, the tests that provide the data to set the specifications must be accurately done. A typical test consists of applying an axial force or cyclic forces to the test specimen to determine the tensile strength or fatigue strength of the specimen. To get an accurate result, the pulling force must act on the bolt directly along its longitudinal axis. The grips that hold either end of the test specimen must therefore be very accurately aligned with the longitudinal axis of the bolt. If the two grips are not so aligned, the forces that are applied to the specimen will not only pull on the specimen, but will also act to bend the specimen. The bending force will not be measured by the sensors that are doing the measurements, because the sensors would be set up to measure only axial forces. Due to misalignments, the applied force may result in significant bending stresses and strains.

The presence of bending forces may lead to significant errors in test results, and contribute to data scatter when a number of repeat tests on identical test specimens are performed. While efforts can be made to make the test frame as precisely aligned as possible, changing grips or setting up a new test spacing may cause the frame to have small misalignments. It is important to realize that extremely small misalignments are a major concern, since such misalignments can easily result in substantial bending stresses being placed on the test specimen.

A test frame typically consists of two parallel columns and a base extending between the two columns. A crosshead is suspended between the two columns and above the base. The crosshead is moveable in the vertical dimension to vary the distance between the base and the crosshead. The distance as set is defined as the test spacing. A load train is interposed between the base and the crosshead. The load train may consist of a lower grip that is affixed to a hydraulic actuator within the base, an upper grip that is affixed to the crosshead, a test specimen that is grasped between the two grips, and a load cell for developing test data on the test specimen. Hydraulic actuation typically provides the required force on the test specimen. The test frame may be designed to perform fatigue, low cycle fatigue, fracture, tensile, compression and bend tests on test specimen and alternatively, the two parallel upright supports may be screws and the crosshead is driven upward on the screws to provide a tensile load on the specimen.

Typically, the crosshead is a massive piece that is designed to slide up and down on the columns in order to adjust the test spacing between the base and the crosshead. A large bore in each side of the crosshead encompasses the respective column. The bores are split longitudinally. Opposing flanges are thus created on either side of the split. A number of large bolts penetrate the opposing flanges. Tightening the bolts clamps the bores on the columns, holding the crosshead in the desired position.

Accordingly, as the crosshead is positioned on the uprights, the crosshead becomes slightly skewed, such that it is not perfectly at right angles with the two columns. The crosshead is therefore not parallel with the base, which leads to the misalignment of the load train. The misalignment may be either angular, lateral, or both, and is reflected as bending in the test specimen.

Moving the crosshead to a new position on the columns, generates misalignments in the test apparatus. Because the heighth dimension of the crosshead is not very great when compared to its lateral dimension, e.g. the distance between the columns, moving the crosshead to a new position and clamping it in position affects the parallelism with the base of the test frame. Further, the columns are not perfectly straight and are not perfectly perpendicular to the base. This contributes to the lack of parallelism with the base.

Devices exist today to correct misalignment in test frames, but their use leads to several problems. Conventional correction devices typically comprise a set of large precision washers, with slight angles on their mating faces. A bolt or stud passes through the assembly of washers and the assembly is placed loosely supporting the upper portion of the load train that is affixed to the crosshead. The two plates have markings on their circumference to locate the angular misalignment between the centerlines of the upper and lower grip assemblies. The set of washers is first rotated to the plane in which angular alignment is to be adjusted. Then, the plates are rotated in opposite directions from each other to change the angular alignment. This causes large lateral displacements. Accordingly, the angle must be adjusted first and then the resulting lateral displacements can be accounted for. Once the angles are adjusted by use of the mating washers, four bolts allow the lateral displacements in two different planes to be adjusted.

The nature of the design requires that the preload stud be loose during adjustment. After both the angular and the lateral misalignments have been adjusted out, the stud is tightened to preload the load train. Tightening this stud frequently causes some shift in the alignment. As a result, an iterative process is required to achieve alignment. This can be time consuming and frustrating for the operator. Furthermore, adjusting the lateral displacement may allow rotation about an undesired position, causing a new angular error in a different axis from the axis of the original error. In some designs, the stud is tightened hydraulically, which simplifies operation, but still frequently produces the shift in alignment upon applying the preload.

A device that would allow a single adjustment of both angular and lateral displacement while the train of devices in the machine was preloaded would be a decided advantage. When used with an existing machine having average accuracy, the results would be a machine in which the train of devices is very accurately aligned and is much easier for the operator to use and promotes a long service life.

SUMMARY OF THE INVENTION

The device of the present invention solves the alignment problems outlined above by allowing the operator to accurately align the train of devices in the machine in a single operation without successive iterations. The alignment device is preloaded by applying a compressive force to keep the alignment device in position. Adjustments are made while the preload is in place. The preload is not released after the alignment is made. Therefore, unlike conventional designs, the alignment is maintained even after adjustments are made, without the need for an iterative process of applying and releasing tension. Furthermore, when used with a test frame, angular adjustment occurs with the center of rotation at approximately the center of the test specimen. The large concentric misalignments that frequently occur while adjusting the angular alignment with conventional systems are thereby avoided. Lateral alignment and angular alignment are adjusted completely independent of one another.

The alignment device hereof broadly comprises four main parts: a center plate, an angular alignment disc, a lateral alignment disc and adjustment devices. The angular alignment disc has a curved face that mates with a curved face on the center plate to produce angular displacement. The lateral alignment disc has a flat face that mates with a flat face on the center plate to produce lateral displacement.

Adjusting screws allow one grip to be moved in four independent axes. Two of the adjustments affect angular displacement about perpendicular axes. The other two adjustments affect the lateral displacement in two perpendicular axes.

BRIEF DESCRIPTION OF THE DRAWINGS

FIG. 5 is a fragmentary view of a test frame depicting an alignment device in accordance with the present invention inserted in the load train, with the load train depicted with an angular displacement;

FIG. 6 is similar to FIG. 5, but with the load train depicted with a lateral displacement;

FIG. 7 is a fragmentary view of a test frame with an alignment device in accordance with the present invention depicted in the load train, with both the angular displacement of FIG. 5 and the lateral displacement of FIG. 6 removed by the alignment devices such that the load train is in alignment;

FIG. 8 is a side perspective of an alternative embodiment of an alignment device with a portion broken away so that details of the preloading mechanism are depicted;

DETAILED DESCRIPTION OF THE DRAWINGS

Figure 1:
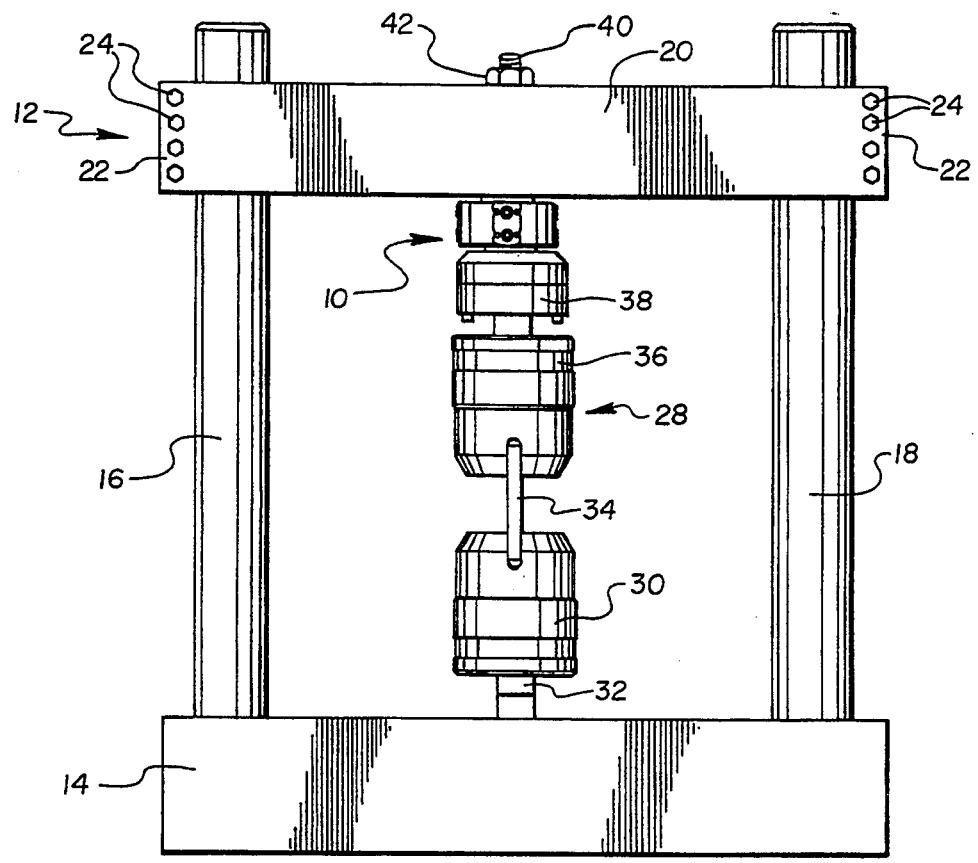
FIG. 1 is an elevational view of a test frame with an alignment device in accordance with the present invention inserted in the load train.

An alignment device 10 in accordance with the present invention is depicted in FIG. 1 in use with a materials test frame 12. Materials test frame 12 has a base 14 that includes a hydraulic actuator and controls (not shown) for applying desired forces to a test specimen. Two spaced apart and parallel columns 16, 18 project upwardly from base 14. A moveable crosshead 20 is slideably carried by columns 16, 18.

Crosshead 20 is designed to slide up and down on columns 16, 18 to provide for the adjustment of the test spacing between crosshead 20 and base 14. Crosshead 20 includes vertical bores at each side that are not shown. Each bore encompasses a respective column 16, 18. The bore structure includes a split at each outer side margin of the crosshead 20, forming a pair of opposed flanges 22 on each end of the crosshead.

Flanges 22 have multiple bores therethrough. Bolts 24 pass through the bores and are secured by nuts (not shown). After properly positioning crosshead 20 with respect to base 14, the nuts on bolts 24 are tightened. Respective flanges 22 are thereby compressed together resulting in compressive frictional engagement of the columns 16, 18 with the internal faces of the bore structure in crosshead 20, rigidly holding crosshead 20 in a selected elevational position on columns 16, 18 above base 14.

A load train 28 is shown positioned between crosshead 20 and base 14. It is understood that other components than those that are shown in the drawings may comprise load train 28. Specifically, in an application that demanded an exceptional degree of accuracy, three alignment devices 10 were utilized in the load train 28 in order to achieve the requisite degree of alignment accuracy. In the particular example shown, load train 28 has a lower grip 30. Lower grip 30 is attached by lower grip base 32 to the hydraulic actuator contained within base 14. Lower grip 30 has jaws that can hydraulically grasp the lower end of a test specimen 34. Test specimen 34 is typically an elongated piece, with a reduced center section about which certain performance data are sought.

The second, upper end of test specimen 34 is grasped by upper grip 36. Upper grip 36 is in turn connected to load cell 38. Load cell 38 contains the sensor that measures axial force on test specimen 34. Load cell 38 generates a signal that is typically sent via electrical conduit to a data storage and control apparatus. Load cell 38 is in turn connected to alignment device 10, which is in turn connected to crosshead 20. Upper grip 36, load cell 38 and alignment device 10 are held in place by a stud 40. Stud 40 passes through crosshead 20 and continues centrally through alignment device 10 and load cell 38 to be affixed to upper grip 36. Stud 40 is held in place by nut 42.

Alignment device 10 broadly includes a central plate 44, angular alignment element 46, lateral alignment element 48, and adjusting screws 72, 82.

Central plate 44 is generally annular, having a central hole 45 large enough to accommodate stud 40. Plate 44 has a curved surface 50 and an opposed flat surface 52. Curved surface 50 is a precision spherical surface. The outer, peripheral portion of plate 44 presents an annular ring 49 having an upwardly directed lip 51 and a downwardly directed lip 53. The surfaces 50 and 52 are centrally located within respective lips 51 and 53. In a preferred embodiment, central plate 44.is formed by relief techniques that leave annular ring 49 as the periphery of plate 44 during the formation of plate 44.

Angular alignment element 46 comprises a disk 47 with a central hole 55 large enough to receive stud 40 with some play about stud 40. Angular alignment element 46 has a first, outwardly directed surface 54 that is generally flat. The opposed surface 56 of angular alignment element 46 is generally curved. Curved surface 56 presents a precision concave curve formed to mate with the convex curve of curved surface 50 of plate 44. The depth of angular alignment element 46 is slightly greater than the depth of the lip 53 of angular ring 49. Accordingly, when curved surface 56 of angular alignment element 46 abuttably engages curved surface 50 of plate 44, the angular alignment element 46 projects outwardly beyond the edge of the lip 53 of angular ring 49. Curved surface 56 of angular alignment apparatus 46 and curved surface 50 of plate 44 can be coated with a low friction coating to facilitate their mutual slidable engagement.

Central hole 55 in angular alignment element 46 is somewhat greater in diameter than the diameter of stud 40 to facilitate the movement of angular alignment element 46 about stud 40 during the angular alignment process. A portion of curved surface 56 of angular alignment apparatus 46 may be scalloped out to create counterbore 58. This is done to ensure that the preload is carried on the outer periphery of the mating parts, so the alignment frame has high lateral stiffness. Counterbore 58 presents outer ring 60 to curved surface 56, ensuring the contact surface between curved surface 56 of angular alignment element 46 and curved surface 50 of plate 44 mate at a large radius.

The origin of the radius of the curve of curved surface 56 of angular alignment element 46 is designed to be located in space approximately along the center of the longitudinal axis of test specimen 34 when alignment device 10 is installed in load train 28. It will be appreciated that in order to take advantage of this design feature, alignment device 10 must be placed in load train 28 with lateral alignment element 48 closest to test specimen 34 and angular alignment element 46 furthest from test specimen 34. Angular alignment element 46 is accordingly always oriented to face away from test specimen 34.

Lateral alignment element 48 comprises a disk 59, having a central hole 62 therethrough to receive stud 40. Central hole 62 is of somewhat greater diameter than the diameter of stud 40 in order to accommodate lateral motion of the alignment device 10 relative to stud 40 during the lateral alignment process.

Lateral alignment element 48 has opposing, generally flat surfaces 64, 68. As depicted in FIG. 1, flat surface 64 is oriented proximal the upper side of load cell. Inwardly facing flat surface 64 slidably engages the flat surface 52 of plate 44. Flat surface 52 of plate 44 or flat surface 64 of lateral alignment element 48 can be coated with a low friction coating to facilitate their mutual slidable engagement. In a preferred embodiment, flat surface 64 of lateral alignment element 48 may be scalloped out to present counterbore 70. Counterbore 70 presents an outer ring 71 of flat surface 64. Outer ring 71 moves the contact surface area to the outer edge between flat surface 64 of lateral alignment element 48 and flat surface 52 of plate 44. The depth of lateral alignment element 48 is greater than the depth of lip 51 of annular ring 49. Lateral alignment element 48 accordingly projects outwardly beyond the lip 51 of annular ring 49.

Four alignment adjusting screws 72 are received within the upward facing lip 53 of annular ring 49 to accomplish the angular alignment process in two angular axes with two opposing screws effective in each of two perpendicular axes. Each adjusting screw 72 is threadably received by a threaded bore 73 in annular ring 49. Threaded bores 73 pass through lip 53 of annular ring 49. A recess 71 is provided in the head of each screw 72 to accommodate an Allen type wrench for turning each screw 72 as desired.

In one embodiment, adjusting screws 72 can act directly on angular adjustment apparatus 46 to position alignment apparatus 46 as desired with respect to plate 54. In the embodiment depicted, sliding blocks 74 are interposed between adjusting screws 72 and angular alignment apparatus 46. Sliding blocks 74 have a curved, beveled face 75 for slideably abutting angular alignment apparatus 46 and an opposed flat face 77 for engaging adjusting screws 72.

Figure 3:
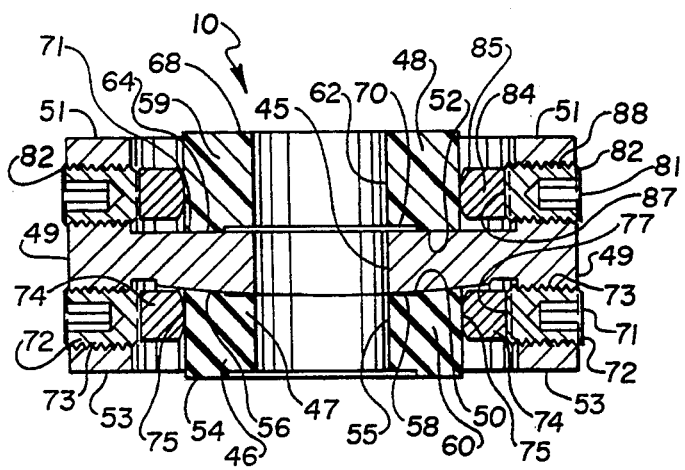
FIG. 3 is a sectional view of the alignment device taken along line 3—3 of FIG. 2.
Figure 4:
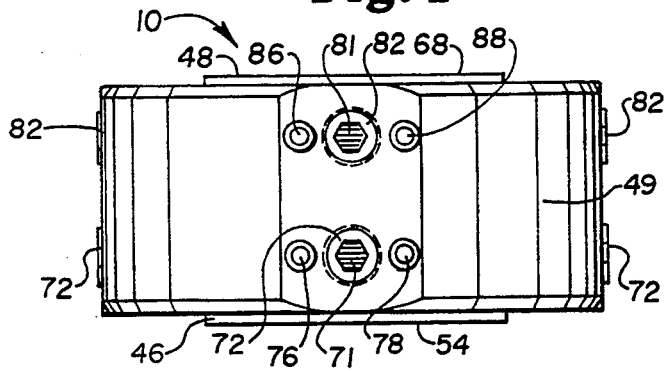
FIG. 4 is a side elevational view of the alignment device.

Sliding blocks 74 are mounted on pins 76, 78. Pins 76, 78 ride in bearing material 80 to facilitate the ease with which sliding block 74 may be moved inward and outward. Sliding blocks 74 are utilized to ensure that there is no rotation of angular alignment apparatus 46 when the angular adjusting screws 72 that are located at 90° from those shown in FIG. 3 are in use. The 90° relationship of such angular adjusting screws 72 is shown in FIG. 4.

Four alignment adjusting screws 82 are received within the downward facing lip 51 of annular ring 49 to accomplish the lateral alignment process in two perpendicular axes with two opposing screws effective in each of two perpendicular axes. Each adjusting screw 82 in threadably received by a threaded bore 83 in annular ring 49. Threaded bores 83 pass through lip 51 of annular ring 49. A recess 81 is provided in the head of each screw 82 to accommodate an Allen type wrench for turning each screw 82 as desired.

Figure 2:
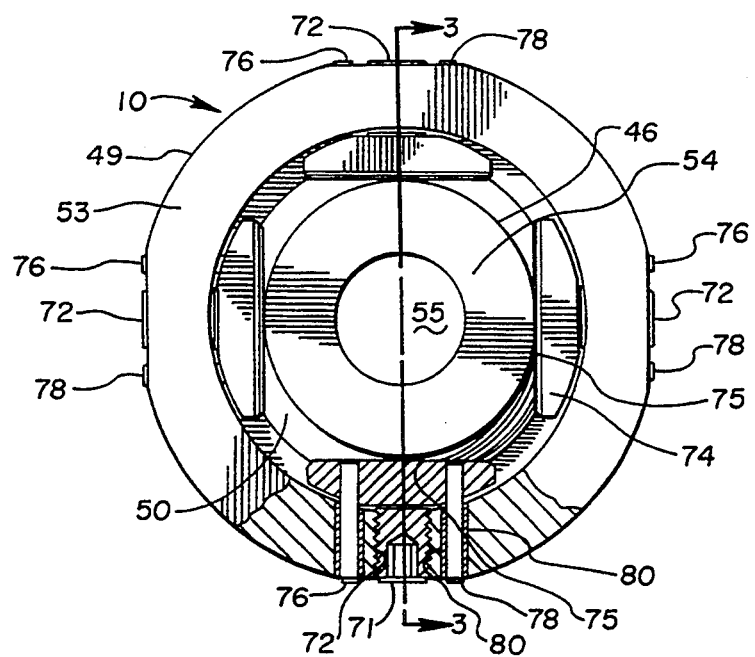
FIG. 2 is a bottom plan view of the alignment device with a portion broken out to show an alignment adjustment screw and block.

In one embodiment, adjusting screws 82 can act directly on lateral adjustment apparatus 48 to position alignment apparatus 48 as desired with respect to plate 44. In the embodiment depicted, sliding blocks 84 are interposed between adjusting screws 82 and lateral alignment apparatus 48. Sliding blocks 84 have a curved, beveled face 85 for slideably abutting lateral alignment apparatus 48 and an opposed flat face 87 for engaging adjusting screws 82. FIG. 2 depicts the sliding blocks 74 in top plan view. Sliding blocks 84, although not shown in plan view, are of similar shape as the sliding blocks 74.

Sliding blocks 84 are mounted on pins 86, 88. Pins 86, 88 ride in bearing material 80 to facilitate the ease with which sliding block 84 may be moved inward and outward. Sliding blocks 84 are utilized to ensure that there is no rotation of angular alignment apparatus 46 when the angular adjusting screws 82 that are located at 90° from those shown in FIG. 3 are in use. The 90° relationship of such angular adjusting screws 82 is shown in FIG. 4.

An alternative embodiment is depicted in FIG. 8. This embodiment is to be used primarily for aligning machinery other than utilized with materials testing equipment. In such applications, there is no central stud through a load train. Accordingly, the alignment device 10 must be internally preloaded. Similar numbers are used to describe similar elements of the design as those that exist in the previously described embodiments.

Alignment device 10 broadly includes a central plate 44, angular alignment element 46, lateral alignment element 48, and adjusting screws 72, 82.

Central plate 44 is generally annular, having a central hole 45 large enough to accommodate stud 40. Plate 44 has a curved surface 50 and an opposed flat surface 52. Curved surface 50 is a precision spherical surface. The outer, peripheral portion of plate 44 presents an annular ring 49 having an upwardly directed lip 51 and a downwardly directed lip 53. The surfaces 50 and 52 are centrally located within respective lips 51 and 53. In a preferred embodiment, central plate 44 is formed by relief techniques that leave annular ring 49 as the periphery of plate 44 during the formation of plate 44.

Angular alignment element 46 comprises a disk 47 with a central hole 55 large enough to receive stud 40 with some play about stud 40. Angular alignment element 46 has a first, outwardly directed surface 54 that is generally flat. The opposed surface 56 of angular alignment element 46 is generally curved. Curved surface 56 presents a precision concave curve formed to mate with the convex curve of curved surface 50 of plate 44. The depth of angular alignment element 46 is slightly greater than the depth of the lip 51 of angular ring 49. Accordingly, when curved surface 56 of angular alignment element 46 abuttably engages curved surface 50 of plate 44, the angular alignment element 46 projects outwardly beyond the edge of the lip 53 of angular ring 49. Curved surface 56 of angular alignment apparatus 46 and curved surface 50 of plate 44 can be coated with a low friction coating to facilitate their mutual slidable engagement.

Central hole 55 in angular alignment element 46 is somewhat greater in diameter than the diameter of stud 40 to facilitate the movement of angular alignment element 46 about stud 40 during the angular alignment process.

Lateral alignment element 48 comprises a disk 59, having a central hole 62 therethrough to receive stud 40. Central hole 62 is of somewhat greater diameter than the diameter of stud 40 in order to accommodate lateral motion of the alignment device 10 relative to stud 40 during the lateral alignment process.

Lateral alignment element 48 has opposing, generally flat surfaces 64, 68. Inwardly facing flat surface 64 slidably engages the flat surface 52 of plate 44. Flat surface 52 of plate 44 or flat surface 64 of lateral alignment element 48 can be coated with a low friction coating to facilitate their mutual slidable engagement. The depth of lateral alignment element 48 is greater than the depth of lip 53 of annular ring 49. Lateral alignment element 48 accordingly projects outwardly beyond the lip 53 of annular ring 49.

The significant difference of the embodiment depicted in FIG. 8 is the provision of structure for internal preloading. To accomplish this, stud 40 has a first threaded end 100. First threaded end 100 is threaded into threaded bore 102 in first collar 104. First collar 104 is disposed in recess 106 in lateral alignment element 48. First collar 104 is sufficiently smaller in periphery than recess 106 to permit a certain amount of play during the alignment process. First collar 104 has an inner curved face 108 that mates with curved bottom 110 of recess 106, the mating interface providing for slight angular rotation of stud 40 during the alignment process.

Stud 40 has a second threaded end 112 that passes through and protrudes beyond a bore 114 in second collar 116. Nut 118 is threaded onto the protruding second threaded end 112. A washer 120 is interposed between nut 118 and second collar 116. Alternatively, a spring (not shown) may be interposed between nut 118 and second collar 116 or interposed between washer 120 and second collar 116.

Second collar 116 is disposed in recess 122 in angular alignment element 46. Second collar 116 is sufficiently smaller in periphery than recess 122 to permit a certain amount of play during the alignment process. Second collar 116 has an inner curved face 124 that mates with curved bottom 126 of recess 122, the mating interface providing for slight angular rotation of stud 40 during the alignment process.

Threaded bores 128 are depicted in surfaces 54, 68 of angular alignment element 46 and lateral alignment element 48 respectively. Bores 128 are adapted to be mated to the machinery in which alignment device 10 is utilized. Such bores 128 or other conventional attachment means may be customized to meet the needs of the particular use of alignment device 10.

In operation, load train 28 is assembled within material test frame 12. It may be necessary to adjust the test spacing to accommodate the desired load train and test specimen by adjusting the height of crosshead 20. A tensioning preload is applied to the upper portion of load train 28 by tightening down on nut 42, carried by stud 40. This is typically done manually using a large torque wrench. The tensioning preload is an important concept that makes the present invention superior to existing apparatus that is designed to perform the same function. The preload permits the load train to be very rigidly fixed before, during, and after the alignment process. There is no slackening once the preload is imposed that introduces error. In the testing of materials, the preload that is applied is always greater than the load that will be imposed on the test specimen during testing. For example, if the test regimen calls for the imposition of 22,000 pounds of force on the test specimen, the nut 42 will be torqued to approximately 25,000 pounds.

FIGS. 5, 6 and 7 depict an alignment sequence related to a skewed crosshead 20 in a test frame 12. It will be appreciated that the displacements shown in FIGS. 5 and 6 are greatly exaggerated for the purpose of illustrating the misalignments. In actuality, the misalignments are physically very small, but are still significant as to their effect on readiness of measurements test specimens. For example, the specifications of one such alignment device 10 provide for a lateral adjustment capability of $+/-0.025$ inch and an angular adjustment capability of $+/-0.25$ degree.

FIG. 5 shows an angular and lateral displacement between the centerline 90 of upper grip 36 and the centerline 92 of lower grip 30. The angular disparity shown must be zeroed out to obtain accurate test results on test specimen 34. The preload is first applied. To accomplish the alignment, the adjusting screws 72 are turned to cause angular alignment apparatus 46 to slide with respect to plate 44. This sliding causes an angular disparity between angular alignment apparatus 46 and plate 44 that accounts for the angular disparity shown in FIG. 5. Without adjusting crosshead 20, the angular disparity between upper grip 36 and lower grip 30 can be removed. It should be realized that this rotation generates a slight bend in stud 40. This bend does not affect the accuracy of the measurements taken across the test specimen, however, because its binding is entirely internal to the upper part of load train 28. Rotation is as indicated by arrow A.

Figure 12:
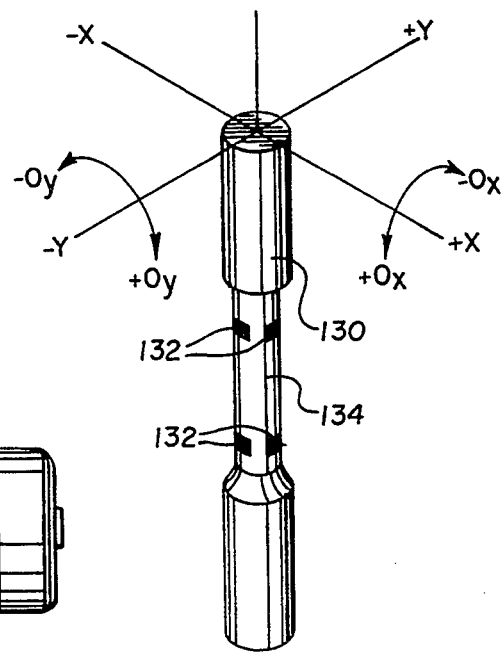

In practice, a test specimen 130 may be subjected to bending stress as indicated in FIG. 12. Bending in either the X plane or the Y plane may be a lateral displacement or an angular displacement or both. As depicted, lateral displacement may be in the $+X$ or $-X$ directions or the $+Y$ or $-Y$ directions. The angular displacement may be in the $+\phi_x$ or $-\phi_x$ directions or the $+\phi_y$ or $-\phi_y$ directions. Measurement of the bending stresses is preferably done by strain gages 132 attached to the specimen gage section 134, the central, narrowed section of test specimen 130. Typically, eight strain gages 132 are applied to the specimen gage section 134, with four strain gages 132 equiangularly disposed around the circumference of specimen gage section 134 at one end of the specimen gage section 134 and four strain gages 132 equiangularly disposed around the circumference of specimen gage section 134 at the other end of the specimen gage section 134. The strain gages 132 are connected in pairs, where the circumferentially opposed strain gages 132 at an end of specimen gage section 134 constitute a pair. Such members of a pair of strain gages 132 are connected to each other in a half bridge configuration. In this way, the strain gages 132 are connected to read bending stresses only and not be sensitive to axial load.

In a preferred embodiment, strain gages 132 are electrically connected to a controller with software designed for the purpose of performing the alignment. Four channels of DC conditioning electronics read the four strain gage pairs into the controller. A scope display is split between two X-Y plots. The first scope display presents the strain gage pairs from the first end of specimen gage section 134 and the second scope display presents the strain gage pairs from the second end of specimen gage section 134. By utilizing adjusting screws 72, 82, a dot display can be adjusted on each scope display. Angular adjustments cause the strain gage display dots on the two X-Y axes to move in the same direction. The angular difference is zero when the gages read equal and opposite signs. Lateral adjustments cause the strain gage display dots on the two X-Y axes to move in opposite directions. The lateral difference is zero when the two dots go to zero on the respective X-Y displays.

The origin of the radius of curved surface 50 of the angular alignment apparatus 46 lies approximately at the center of the test specimen 34. Thus, when adjusting the angular alignment, an angular displacement is imposed on the test specimen 34 with little change in the lateral concentricity. If the origin of the radius were located elsewhere, angular change would move the origin off the centerline of the load train 28 and thereby introduce an additional lateral error. The placement of the origin at the center of the test specimen 34 is therefore important to maintaining the new independence of the angular and lateral alignment adjustments.

Once the angular adjustments are set, the lateral adjustments are used to set the lateral concentricity. FIG. 6 shows a lateral displacement between centerline 90 of upper grip 36 and centerline 92 of lower grip 30. In the depiction of FIG. 6, centerline 92 is to the left of centerline 90. Utilizing adjusting screws 82, lateral alignment apparatus 48 is made to slide with respect to plate 54. This sliding results in a lateral displacement between lateral alignment apparatus 48 and plate 44 that removes the misalignment shown in FIG. 6. The motion is as indicated by arrow B. The adjustments described may be repeated using the adjusting screws 82 that are located 90° from those previously described.

A strain-gaged specimen is normally used to monitor the alignment process. However, other measuring devices could also be used. Typically, the strain-gaged specimen has eight strain gages, four at one end of the gage section and four at the opposite end of the gage section, with each set of four equally spaced apart from each other in 90 degree increments to provide for proper determination of both angular and lateral misalignments. By reading the output of these strain gages, it is thus possible to determine which adjustments need to be made to the alignment. The use of such shain gaged specimens is well known in the art.

FIG. 7 depicts the effects of both the angular rotation indicated by arrow A in FIG. 5 and the lateral displacement indicated by arrow B in FIG. 6. Centerline 90 of upper grip 36 and centerline 92 of lower grip 30 are coincident in FIG. 7. When the tests are performed on test specimen 34, there will be no bending forces on test specimen 34 to affect the results of the test.

Figure 9:
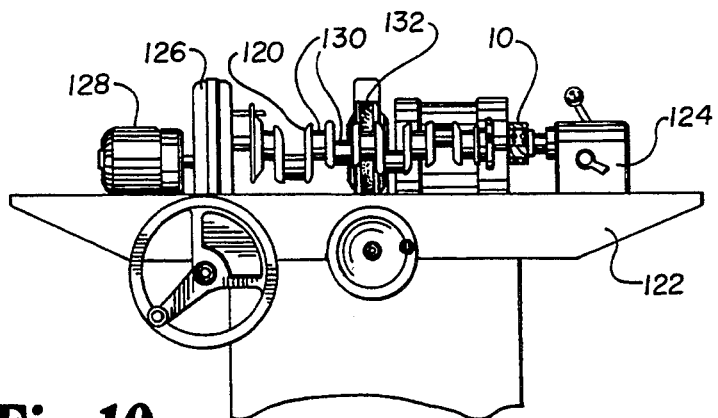
FIG. 9 is a side perspective of an alignment device installed in a lathe.
Figure 10:
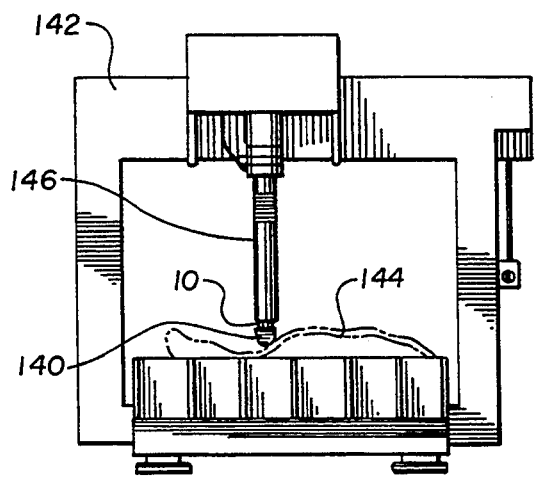
FIG. 10 is a side perspective of an alignment device installed in a press.
Figure 11:
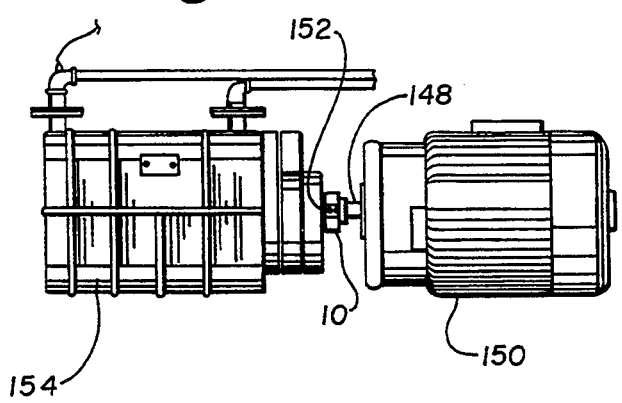
FIG. 11 is a side perspective of an alignment device installed in on the output shaft of an electric motor and connected to the input shaft of a pump; and, FIG. 12 is a perspective view of a test specimen utilized in a materials test apparatus showing the axes of angular and lateral bending stress and the placement of sensors to sense the bending stress.

Operationally, the alignment device 10 depicted in FIG. 8 is first subjected to the preload by tightening down on nut 118 and thereby putting plate 44, angular alignment element 46, and later alignment element 48 in a desired amount of compression. The alignment device 10 is then installed in the machinery in which it is to be utilized. Typical installations are depicted in FIGS. 9, 10, and 11. As shown, the usage may be to better align rotating axes in especially large machines where maintaining accurate alignment becomes difficult. The required alignment precision is easily built into smaller versions of the same machines. In the scale up to the very large machines, the mere physical size makes it difficult to achieve the desired degree of alignment.

As shown in FIG. 9, the alignment device 10 is utilized to align the workpiece, in this case, crankshaft 120, in a grinding lathe 122. Alignment device 10 is interposed between tail stock 124 and an end of crankshaft 120. The other end of crankshaft 120 is held firmly by rotation unit 126, which is powered by motor 128. Such alignment ensures the accuracy of the journals 130 as ground by grinding wheel 132.

FIG. 10 depicts the alignment device 10 utilized to align the ram head 140 in a press 142. Despite the large size, extreme accuracy is needed in some shaping of the workpiece 144. Due to the length of the ram 146, certain misalignments in the ram head 140 are introduced as the ram 146 is lowered. By interposing alignment device close to the workpiece 144, these misalignments can be eliminated.

FIG. 11 depicts the alignment device 10 utilized in an application to align the output shaft 148 of an electric motor 150 and the input shaft 152 of an industrial pump 154. Again as size increases, it is more difficult to maintain accurate alignment of the pump 154 and the motor 150. Inaccuracies in alignment are introduced through the separate mountings of the pump 154 and the motor 150. Such mountings are usually by bolt through the relatively coarsely drilled holes that are necessary to accommodate large bolts. Accurate alignment of output shaft 148 and input shaft 152 is necessary to smooth running and prolonged life of the bearings of motor 150 and pump 154. Other applications of the invention will be apparent to those skilled in the art.

What is claimed is:

1. An alignment device for use in a materials test frame, the test frame including means for applying an axial force to a load train, the load train including a test specimen having an axial dimension and sensing apparatus to measure various parameters of the test specimen responsive to the force, first and second gripping means for holding the test specimen in the load train during testing, each such gripping apparatus presenting a respective first and second gripping axis, said load train being in a preload condition wherein the preload applied exceeds the axial force to be applied to the test specimen, said alignment device comprising:

first alignment means for angularly aligning the first and second gripping axes operably slideably coupling said first gripping means to said test frame, having a curved surface, the origin of the radius of said curved surface being located proximate the center of the axial dimension of the test specimen, such that sliding motion of the first alignment means about such curved surface with respect to said test frame produces an angular shift between said first and second gripping axes;

second alignment means for laterally aligning the first and second gripping axes operably coupling said second gripping means to said test frame, having a fiat surface, such that sliding motion along said flat surface of the second alignment means with respect to said test frame produces a lateral shift between said first and second gripping axes; and isolation means operably coupling and interposed between said first and second alignment means for isolating said first alignment means from said second alignment means such that the angular rotation about the center of the axial dimension of the test specimen and lateral relative shifting of said first and second axes is accomplished substantially independently of each other.

2. An alignment device as claimed in claim 1, wherein the isolation means comprises a plate having first and second generally opposed surfaces, the first surface being generally curved to cooperatively engage the curved surface of said first alignment means and the second surface being generally flat to cooperatively engage the fiat surface of said second alignment means.

3. An alignment device as claimed in claim 2, wherein the first alignment means comprises a disc having a first surface that is generally curved, said generally curved surface being complementarily engageable with said generally curved first surface of the isolation means.

4. An alignment device for use in a materials test frame as claimed in claim 2, wherein the second alignment means comprises a disc having a first surface that is generally flat, said generally flat surface being complementarily engageable with said generally flat second surface of the isolation means.

5. An alignment device for use in a materials test frame as claimed in claim 2 wherein the isolation means further comprises an annular ring operably coupled to the outer periphery of the plate and defining first and second opposing lips on said plate, each of said first and second lips having a set of four equally spaced threaded bores around the respective lip, and the adjustment means comprising a screw threaded in each of said bores, each screw in the set of bores of said first lip having a first end adapted to rotate said screw in said threaded bore and a second end in operable engagement with said first alignment means and adapted for exerting a force thereon generally perpendicular to said first and second gripping axes.

6. An alignment device as claimed in claim 1, further including adjustment means moveable in two lateral planes and in two angular planes and in operable engagement with the first alignment means for effecting said angular shift between said first and second axes and in operable engagement with the second alignment means for effecting said lateral shifts between said first and second axes.

7. An alignment device for accurately axially aligning a machinery train having an axial dimension, the machinery train being under a preloaded condition and having a first portion defining a first portion axis and a second portion defining a second portion axis, said second portion coarsely in line with and spaced apart from said first portion, coupling means for operably, slideably coupling said first portion of the machinery train to said second portion of the machinery train with the alignment device interposed therebetween, the alignment device comprising:

first alignment means having a curved surface, the origin of radius of said curved surface being located proximate the center of the axial dimension of the machinery train for angularly aligning said first and second portion axes such that sliding motion of the first alignment means with respect to said first and second portions of the machinery train produces an angular shift between said first and second portion axes;

second alignment means for laterally aligning said first and second portion axes such that sliding motion of the second alignment means with respect to said first and second portions of the machinery train produces an lateral shift between said first and second portion axes; and isolation means operably coupling and interposed between said first and second alignment means for isolating said first alignment means from said second alignment means such that the angular rotation about the center of the axial dimension of the machinery train and lateral relative shifting of said first and second portion axes is accomplished substantially independently of each other.

8. An alignment device as claimed in claim 7, wherein the isolation means comprises a plate having first and second generally opposed surfaces, the first surface being generally curved to cooperatively engage the curved surface of said first alignment means and the second surface being generally flat to cooperatively engage the flat surface of said second alignment means.

9. An alignment device as claimed in claim 8, wherein the first alignment means comprises a disc having a first surface that is generally curved, said generally curved surface being complementarily engageable with said generally curved first surface of the isolation means.

10. An alignment device for accurately aligning a machinery train as claimed in claim 8, wherein the second alignment means comprises a disc having a first surface that is generally flat, said generally flat surface being complementarily engageable with said generally flat second surface of the isolation means.

11. An alignment device for accurately aligning a machinery train as claimed in claim 8 wherein the isolation means further comprises an annular ring operably coupled to the outer periphery of the plate and defining first and second opposing lips on said plate, each of said first and second lips having a set of four equally spaced threaded bores around the respective lip, and the adjustment means comprising a screw threaded in each of said bores, each screw in the set of bores of said first lip having a first end adapted to rotate said screw in said threaded bore and a second end in operable engagement with said first alignment means and adapted for exerting a force thereon generally perpendicular to said first and second gripping axes.

12. An alignment device as claimed in claim 7, further including adjustment means moveable in two lateral planes and in two angular planes and in operable engagement with the first alignment means for effecting said angular shift between said first and second axes and in operable engagement with the second alignment means for effecting said lateral shifts between said first and second axes.

13. An alignment device for use in a materials test frame, the test frame including means for applying an axial force to a load train, the load train including a test specimen having an axial dimension and sensing apparatus to measure various parameters of the test specimen responsive to the force, first and second gripping means for holding the test specimen in the load train during testing, each such gripping apparatus presenting a respective first and second gripping axis said load train being in a preload condition wherein the preload applied exceeds the axial force to be applied to the test specimen, said alignment device comprising:

first alignment means for angularly aligning the first and second gripping axes operably slideably coupling said first gripping means to said test frame, having a curved surface, the origin of the radius of said curved surface being located proximate the center of the axial dimension of the test specimen, such that sliding motion of the first alignment means about such curved surface with respect to said test frame produces an angular shift between said first and second axes;

second alignment means for laterally aligning the first and second gripping axes operably coupling said second gripping means to said test frame, having a flat surface, such that sliding motion along said flat surface of the second alignment means with respect to said test frame produces a lateral shift between said first and second gripping axes; and isolation means operably coupling and interposed between said first and second alignment means for isolating said first alignment means from said second alignment means such that the angular rotation about the center of the axial dimension of the test specimen and lateral relative shifting of said first and second axes is accomplished substantially independently of each other, comprising a plate having first and second generally opposed surfaces, the first surface the first surface being generally curved to cooperatively engage the curved surface of said first alignment means and the second surface being generally flat to cooperatively engage the flat surface of said second alignment means and having an annular ring operably coupled to the outer periphery of the plate and defining first and second opposing lips on said plate, each of said first and second lips having a set of four equally spaced threaded bores around the respective lip, and the adjustment means comprising a screw threaded in each of said bores, each screw in the set of bores of said first lip having a first end adapted to rotate said screw in said threaded bore and a second end in operable engagement with said first alignment means and adapted for exerting a force thereon generally perpendicular to said first and second gripping axes.

14. An alignment device for accurately axially aligning a machinery train having an axial dimension, the machinery train being under a preloaded condition and having a first portion defining a first portion axis and a second portion defining a second portion axis, said second portion coarsely in line with and spaced apart from said first portion, coupling means for operably, slideably coupling said first portion of the machinery train to said second portion of the machinery train with the alignment device interposed therebetween, the alignment device comprising:

first alignment means having a curved surface, the origin of radius of said curved surface being located proximate the center of the axial dimension of the machinery train for angularly aligning said first and second portion axes such that sliding motion of the first alignment means with respect to said first and second portions of the machinery train produces an angular shift between said first and second portion axes;

second alignment means for laterally aligning said first and second portion axes such that sliding motion of the second alignment means with respect to said first and second portions of the machinery train produces an lateral shift between said first and second portion axes; and isolation means operably coupling and interposed between said first and second alignment means for isolating said first alignment means from said second alignment means such that the angular rotation about the center of the axial dimension of the machinery train and lateral relative shifting of said first and second portion axes is accomplished substantially independently of each other, the isolation means comprising a plate having first and second generally opposed surfaces, the first surface being generally curved to cooperatively engage the curved surface of said first alignment means and the second surface being generally flat to cooperatively engage the flat surface of said second alignment means and having an annular ring operably coupled to the outer periphery of the plate and defining first and second opposing lips on said plate, each of said first and second lips having a set of four equally spaced threaded bores around the respective lip, and the adjustment means comprising a screw threaded in each of said bores, each screw in the set of bores of said first lip having a first end adapted to rotate said screw in said threaded bore and a second end in operable engagement with said first alignment means and adapted for exerting a force thereon generally perpendicular to said first and second gripping axes.

* * * * *

UNITED STATES PATENT AND TRADEMARK OFFICE
CERTIFICATE OF CORRECTION

PATENT NO. : 5,377,549
DATED : January 3, 1995
INVENTOR(S) : F. David Werner

It is certified that error appears in the above-indentified patent and that said Letters Patent is hereby corrected as shown below:

Col. 5, line 28, delete "." after -- 44 --;

Col. 14, line 1, delete "fiat" and insert --flat--;

Signed and Sealed this

Thirteenth Day of February, 1996

Attest:

BRUCE LEHMAN

Attesting Officer

Commissioner of Patents and Trademarks